US006291479B1

(12) United States Patent
Sharif

(10) Patent No.: US 6,291,479 B1
(45) Date of Patent: Sep. 18, 2001

(54) USE OF NR2B-SELECTIVE NMDA-RECEPTOR ANTAGONISTS FOR THE TREATMENT OF OPHTHALMIC DISEASES

(75) Inventor: Najam Sharif, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/452,004

(22) Filed: Nov. 30, 1999

Related U.S. Application Data

(60) Provisional application No. 60/110,984, filed on Dec. 3, 1998.

(51) Int. Cl.$^7$ .................................................. A67K 31/445
(52) U.S. Cl. ............................................ 514/317; 514/912
(58) Field of Search ...................................... 514/317, 912

(56) References Cited

U.S. PATENT DOCUMENTS 4,550,022   10/1985   Garabedian et al. ................. 424/127

OTHER PUBLICATIONS

Ambati, et al., Elevated GABA, Glutamate, and VEGF in the Vitreous of Humans With Proliferative Diabetic Retinopathy, *Invest. Ophthalmol. Vis. Sci.*, vol. 38, No. 4 (3234) p. S771 (1997).
Avenet et al., Antagonist properties of the stereoisomers of ifenprodil at NR1A/NR2A and NR1A/NR2B subtype of the NMDA receptor expressed in Xenopus oocytes. *Eur. J. Pharmacology*, vol. 296, pp. 209–213 (1996).
Benveniste et al., Elevation of the Extracellular Concentrations of Glutamate and Aspartate in Rat Hippocampus During Transient Cerebral Ischemia Monitored by Intracerebral Microdialysis, *Journal of Neurochemistry*, vol. 43, No. 5, pp. 1369–1374 (1984).
Carter et al., Non–competitive NMDA receptor antagonists acting on the polyamine site *Excitatory Amino Acid Antagoinists* (Meldrum, B.S., ed), pp. 130–163. Blackwell Scientific Publications, Oxford (1991).
Choi, Excitotoxic Cell Death, *Journal of Neurobiology*, vol. 23, No. 9, pp. 1261–1276 (1992).
Choi, Glutamate Neurotoxicity and Diseases of the Nervous System, *Neuron*, vol. 1, pp. 623–634 (1988).
David et al., Involvement of Excitatory Neurotransmitters in the Damage Produced in Chick Embryo Retinas by Anoxia and Extracellular High Potassium, *Experimental Eye Research*, vol. 46, pp. 657–662 (1988).
Fischer et al., Ro 25–6981, a Highly Potent and Selective Blocker of N–Methyl–D–aspartate Receptors Containing the NR2B Subunit. Characterization in Vitro.,*J. Pharmacol. Expt. Ther.*, vol. 283, pp. 1285–1292 (1997).
Hudson, et al., Short–Wavelength and White–on–White Automated Static Perimetry in Patients With Clinically Significant Diabetic Macular Oedema (DMO), *Invest. Ophthalmol. Vis. Sci.*, vol. 38, No. 4 (3552–B153) p. S768 (1997).

Kew et al., State–dependent NMDA receptor antagonism by Ro 8–4304, a novel NR2B selective, non–competitive, voltage–independent antagonist. *Brit. J. Pharmacology*, vol. 123, pp. 463–472 (1998).
Kutsuwada et al., Molecular diversity of the NMDA receptor channel. *Nature*, vol. 358, pp. 36–41 (1992).
Lieth, et al., Glial Glutamate to Glutamine Conversion is Impaired in Retinas of Diabetic Rats, *Invest. Ophthalmol. Vis. Sci.*, vol. 38, No. 4 (3571–B172) p. S695 (1997).
Massey, S., Cell Types Using Glutamate as a Neurotransmitter in the Vertebrate Retina, N.N. Osborne and G.J. Chader (Eds.) *Progress in Retinal Research*, Chapter 11, Pergammon Press: Oxford, pp. 399–425 (1990).
Menniti et al., CP–101,606, a potent neuroprotectant selective for forebrain neurons. *Eur. J. Pharmacology*, vol. 331, pp. 117–126 (1997).
Miller et al., Excitatory Amino Acid Receptors In The Vertebrate Retina, in *Retinal Transmitters and Modulators: Models for the Brain*, (W.W. Morgan, Ed.) CRC Press, Inc., Boca Raton, II:123–160 (1985).
Olney et al., The Role Of Specific Ions In Glutamate Neurotoxicity, *Neuroscience Letters*, vol. 65, pp. 65–71 (1986).
*Ophthalmic Surgery: Principles of Practice*, Ed., G.L. Spaeth, W.B. Sanders Co., Philadelphia, PA, U.S.A. pp. 85–87 (1990).
Scatton et al., Eliprodil Hydrochloride, *Drugs of the Future*, vol. 19, No. 10, pp. 905–909 (1994).
Sheardown et al., 2,3–Dihydroxy–6–nitro–7–sulfamoyl–benzo(F)quinoxaline: A Neuroprotectant for Cerebral Ischemia, *Science*, vol. 247, pp. 571–574 (1990).
Siesjö, Calcium, Excitotoxins, and Brain Damage, *NIPS*, vol. 5, pp. 120–125 (1990).
Siliprandi et al., N–methyl–D–aspartate–induced neurotoxicity in the adult rat retina, *Visual Neuroscience*, vol. 8, pp. 567–573 (1992).
Sisk et al., Histologic changes in the inner retina of albino rats following intravitreal injection of monosodium L–glutamate, *Graefe's Archive for Clinical and Experimental Ophthalmology*, vol. 223, pp. 250–258 (1985).
Sucher et al., N–methyl–D–aspartate antagonists Prevent Kainate Neurotoxicity in Rat Retinal Ganglion Cells in vitro, *Journal of Neuroscience*, vol. 11, No. 4, pp. 966–971 (1991).
Tung et al., A quantitative analysis of the effects of excitatory neurotoxins on retinal ganglion cells in the chick, *Visual Neuroscience*, vol. 4, pp. 217–223 (1990).
Williams, Ifenprodil Discriminates Subtypes of the N–Methyl–D–aspartate Receptor: Selectivity and Mechanisms at Recombinant Heteromeric Receptors, *Molecular Pharmacology*, vol. 44, pp. 851–859 (1993).

*Primary Examiner*—Zohreh Fay
(74) *Attorney, Agent, or Firm*—Sally S. Yeager

(57) ABSTRACT

The invention is directed to the use of improved NR2B antagonists for the prevention and treatment of retinal or optic nerve head damage in mammals. Compositions and methods are disclosed.

4 Claims, No Drawings

USE OF NR2B-SELECTIVE NMDA-RECEPTOR ANTAGONISTS FOR THE TREATMENT OF OPHTHALMIC DISEASES

This application claims priority to provisional application Ser. No. 60/110,984 filed Dec. 3, 1998.

The present invention relates to methods of treating ophthalmic diseases with NR2B-selective-NMDA-receptor antagonists. In particular, the methods of the present invention are useful in treating glaucoma, macular degeneration and other degenerative diseases of the eye.

BACKGROUND OF THE INVENTION

Retinal or optic nerve head damage, which can result in the loss of vision, is caused by trauma and various pathological events such as ischemia, hypoxia, or edema.

Retinal or optic nerve head ischemia or hypoxia occurs when the blood supply is significantly reduced to those tissues. Ischemia is a complex pathological episode involving numerous biochemical events. In recent years, the involvement of excitatory amino acids in ischemia-related neuronal and retinal damage has been implicated. (See, Choi, *Excitatory cell death, Journal of Neurobiology*, volume 23, pages 1261–1276 (1992); Tung et al., *A quantitative analysis of the effects of excitatory neurotoxins on retinal ganglion cells in the chick, Visual Neuroscience*, volume 4, pages 217–223 (1990); Sisk et al., *Histologic changes in the inner retina of albino rats following intravitreal injection of monosodium L-glutamate, Graefe's Archive for Clinical and Experimental Ophthalmology*, volume 223, pages 250–258 (1985); Siliprandi et al., *N-methyl-D-aspartate-induced neurotoxicity in the adult rat retina, Visual Neuroscience*, volume 8, pages 567–573 (1992); and David et al., *Involvement of excitatory neurotransmitters in the damage produced in chick embryo retinas by anoxia and extracellular high potassium, Experimental Eye Research*, volume 46, pages 657–662 (1988).)

During ischemia or hypoxia, excitatory amino acid levels are markedly elevated in neural tissue (Benveniste et al., *Elevation of the extracellular concentrations of glutamate and aspartate in rat hippocampus during transient cerebral ischemia monitored by intracerebral microdialysis, Journal of Neurochemistry*, volume 43, pages 1369–1374 (1984)), which may lead to excessive stimulation of post-synaptic excitatory amino acid receptors, and potentially result in cell injury. Release of excitatory amino acids has been reported to cause cytotoxicity due to increasing intracellular calcium levels, which in turn affect protein phosphorylation, proteolysis, lipolysis, and ultimately can result in cell death. (See, Choi, *Glutamate neurotoxicity and diseases of the nervous system, Neuron*, volume 1, pages 623–634 (1988); Siesjo, *Calcium, excitotoxins, and brain damage, NIPS*, volume 5, pages 120–125 (1990) and Olney et al., *The role of specific ions in glutamate neurotoxicity, Neuroscience Letters*, volume 65, pages 65–71 (1986).)

Antagonists against excitatory amino acid receptors have been shown to reduce neuronal and retinal damage in ischemic conditions. (See, Sheardown et al., 2,3-*Dihydroxy-6-nitro-7-sulfamoyl-benzo(F)quinoxaline: a neuroprotectant for cerebral ischemia, Science*, volume 247, pages 571–574 (1990); Scatton et al., *Eliprodil Hydrochloride, Drugs of the Future*, volume 19, pages 905–909 (1994); and Sucher et al., *N-methyl-D-aspartate antagonists prevent kainate neurotoxicity in rat retinal ganglion cells in vitro, Journal of Neuroscience*, volume 11, pages 966–971 (1991).)

Diabetic retinopathy is an ophthalmic disease leading to impaired vision and even total blindness. It has been reported that glutamate excitotoxicity has played a role in such vision loss. (See, Ambati, et al., *Elevated GABA, Glutamate, and VEGF in the Vitreous of Humans With Proliferative Diabetic Retinopathy, Invest. Ophthalmol. Vis. Sci.*, volume 38, page S771 (1997), (elevated levels of glutamate in vitreous samples obtained from patients with proliferative diabetic retinopathy who underwent pars plana vitrectomy were reported with the suggestion that these levels of glutamate are potentially toxic to retinal ganglion cells.); Lieth, et al., *Glial Glutamate to Glutamine Conversion is Impaired in Retinas of Diabetic Rats, Invest. Ophthalmol. Vis. Sci.*, volume 38, page S695 (1997), (glial glutamate to glutamine conversion was reported to be impaired in the retinas of diabetic rats.); and Hudson, et al., *Short-Wavelength and White-on-White Automated Static Perimetry in Patients With Clinically Significant Diabetic Macular Oedema (DMO), Invest. Ophthalmol. Vis. Sci.*, volume 38, page S768 (1997), (deficits in retinal function related to ganglion cell function were reported in patients with diabetic macular edema).)

There are at least three ionotropic neuronal receptors associated with excitotoxicity. These receptors have been classified by the agonists that preferentially activate the receptor: N-methyl-D-aspartate (NMDA); kainate; and AMPA (2-amino-3-(3-hydroxy-5-methylisoxazol-4-yl) propanoic acid). These neuronal receptors are differentially distributed to specific cells in the retina. (See, generally, Massey, S., *Cell types using glutamate as a neurotransmitter in the vertebrate retina*, N. N. Osborne and G. J. Chader (Eds.) *Progress in Retinal Research*, Chapter 9, Pergammon Press: Oxford, 399–425 (1990); and Miller et al., *Excitatory amino acid receptors in the vertebrate retina*, in *Retinal Transmitters and Modulators: Models for the Brain*, (W. W. Morgan, Ed.) CRC Press, Inc., Boca Raton, II:123–160 (1985).) The localization of such receptors may account for the pathologies associated with glaucoma or retinal ischemia. For example, death of the retinal ganglion cell has been correlated with the NMDA receptor. (See Sucher et al., *N-methyl-D-aspartate antagonists prevent kainate neurotoxicity in retinal ganglion cells in vitro, J. Neurosci.*, volume 11, issue 4, pages 966–971 (1991).)

The NMDA receptor is further comprised of several subunit proteins. These heteromeric assemblies contain NMDR1 subunits together with one or more of four NR2 subunits (NR2A, B, C and D) in a pentameric assembly of uncertain stoichiometry (Kutsuwada et al., *Molecular diversity of the NMDA receptor channel. Nature*, volume 358, pages 36–41 (1992)). The NR2B subunit of the NMDA receptor is a potential target by which some or all of the neuroprotective effects of certain compounds may be mediated (see, e.g., Fischer et al., *RO-25-6981, a highly potent and selective blocker of N-methyl-D-aspartate receptors containing the NR2B subunit. Characterization in vitro. J. Pharmacol. Expt. Ther.*, volume 283, pages 1285–1292 (1997)).

Various ligands bind the NR2B subunit. For example, ifenprodil and its stereoisomers have been claimed to bind to the NR2B receptor subunit (Avenet et al., *Antagonist properties of the stereoisomers of ifenprodil at NR1A/NR2A and NR1A/NR2B subtypes of the NMDA receptor expressed in xenopus oocytes. Eur. J. Pharmacology*, volume 296, pages 209–213 (1996)). It is believed that selective blockade of the NR2B subunit may prevent the sequence of neurotoxic events following over activation of the NMDA receptor by elevated levels of glutamate.

NMDA receptor antagonists have been pursued in the art for neuroprotection. Given the numerous insults on a cell during ischemia and other trauma, however, the use of NMDA receptor antagonists alone may not provide the cytoprotective efficacy necessary to avoid neurodegeneration. There is a need, therefore, for compounds with broader inhibitory roles, i.e., compounds with dual pharmacophore efficacy, that may provide the added cytoprotective efficacy needed to prevent, reduce or ameliorate neuronal degradation.

SUMMARY OF THE INVENTION

The present invention is directed to compositions and methods of treating ophthalmic diseases. The methods involve the administration to a mammal suffering from, or at risk of, retina or optic nerve head damage, a composition comprising an effective amount of a NR2B -selective NMDA-receptor antagonist having dual pharmacophore efficacy. The methods are particularly suited for the treatment of glaucoma, macular degeneration and other retinal diseases.

DETAILED DESCRIPTION OF THE INVENTION

The present invention provides compositions containing NR2B-selective NMDA -receptor antagonists and methods of use in treating ophthalmic diseases. The activation of the NMDA receptor results in the coordinated assembly of the different subunits to form the cation conducting channel which permits the movement of sodium and calcium ions from the extracellular domain to the cell interior. Excessive stimulation and gating of these cations results in disruption of electrolyte homeostasis, generation of reactive free radicals, and activation of intracellular proteases, ultimately leading to cell death.

During excitotoxic conditions, over-stimulation of the NR2B subunit and, hence, the NMDA receptor, eventually leads to cell death. During ischemic/hypoxic conditions involving neural tissue, a reduction in extracellular oxygen levels occur near the neurons. This reduction results in a shortage of cellular energy derived from ATP, and a disruption of cellular homeostasis. Such deprivation and disruption causes the release of glutamate and other toxic mediators, such as cytokines, resulting in cellular damage and death. Hypoxia also causes rapid efflux of potassium and influx of calcium, chloride and water, thereby causing cellular swelling and eventual death. The influx of calcium during hypoxia also activates various proteases, lipases and kinases which also can cause cell death. Evidence of such effects include cellular membrane lipid peroxidation, lactate dehydrogenase release and intracellular calcium release.

The present invention provides improved NR2B antagonists. The improved NR2B antagonists exhibit antagonism of the NMDA receptor via antagonism of the NR2B receptor and also exhibit anti-hypoxia/ischemia efficacy. The phrase "anti-hypoxia/ischemia efficacy," refers to the cytoprotective activity of the compounds of the present invention against hypoxia/ischemia insults. While not intending to be bound by any theory, it is believed that the improved NR2B antagonists possess anti-hypoxia/ischemia efficacy due to their inhibition of one or more of the hypoxia/ischemia-mediated, deleterious cellular events described above. Since neuronal degredation may result from both hypoxia/ischemia and excitotoxicity events, the improved NR2B antagonists of the present invention provide a two-prong approach to the treatment of ophthalmic neurodegenerative diseases. As used herein, "improved NR2B antagonists" refer to those compounds which inhibit the activation of the NR2B receptor and which also exhibit anti-hypoxia/ischemia efficacy.

Several improved NR2B receptor antagonists of the present invention have been elucidated thus far. Examples of improved NR2B receptor antagonists include:

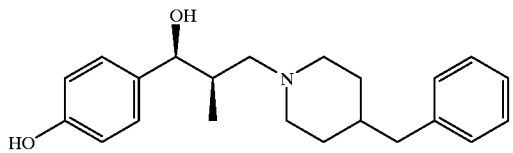

4-benzyl-1-(3-hydroxy-3-(4-hydroxyphenyl)-2-methyl-propyl)piperidine ("RO-25-6981");

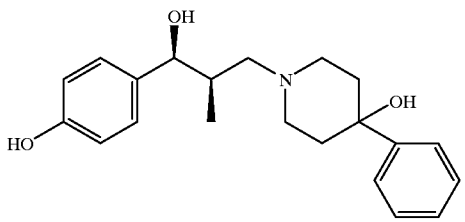

4-hydroxy-1-(3-hydroxy-3-(4-hydroxyphenyl)-2-methyl-propyl)-4-phenylpiperidine ("CP-101-606"); and

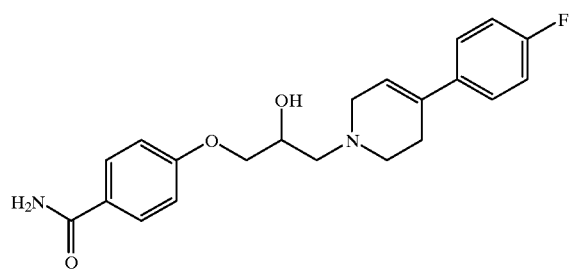

4-{3-[4-(fluoro-phenyl)-3,6-dihydro-2H-pyridin-1-yl]-2-hydroxy-propxy}benzamide ("RO-8-4304").

For further background of the compounds illustrated above, see generally, Menniti et al. *CP-101,606, a potent neuroprotectant selective for forebrain neurons. Eur. J. Pharmacology*, volume 331, pages 117–126 (1997); Fisher et al., *RO-25-6981, a highly potent and selective blocker of N-methyl-D-aspartate receptors containing the NR2B subunit. Characterization in vitro. J. Pharmacology & Experimental Therapeutics*, volume 283, pages 1285–1292 (1997); and Kew et al., *State-dependent NMDA receptor antagonism by RO-8-4304, a novel BR2B selective, non-competitive, voltage-independent antagonist. Brit. J. Pharmacology*, volume 123, pages 463–472 (1998); the foregoing publications are incorporated herein by reference.

RO-25-6981 and RO-8-4304 are preferred improved NR2B antagonists of the present invention.

Other improved NR2B antagonists of the present invention may be elucidated using methods described in the foregoing publications, as well as those disclosed in the following publications:

(1) Williams, *Ifenprodil discriminates subtypes of the N-methyl-D-aspartate receptor: selectivity and mechanisms at recombinant heteromeric receptors. Molecular Pharmacology*, volume 44, pages 851–859 (1993));

(2) Avenet et al., *Antagonist properties of the stereoisomers of ifenprodil at NR1A/NR2A and NR1A/NR2B subtypes of the NMDA receptor expressed in xenopus oocytes. Eur. J. Pharmacology*, volume 296, pages 209–213 (1996));

(3) Carter et al., *Non-competitive NMDA receptor antagonists acting on the polyamine site. Excitatory Amino Acid Antagonists* (Meldrum, B. S., ed), pp. 130–163. Blackwell Scientific Publications, Oxford (1991)); and (4) Fischer et al., *RO-25-6981, a highly potent and selective blocker of N-methyl-D-aspartate receptors containing the NR2B subunit. Characterization in vitro. J. Pharmacol. Expt. Ther.*, volume 283, pages 1285–1292 (1997)); the foregoing publications are incorporated herein by reference.

The improved NR2B antagonists may be obtained commercially or may be prepared by methods known to those skilled in the art.

The methods of the present invention are particularly directed to the use of NR2B antagonists for the treatment of diseases and disorders of the retina, particularly age related macular degeneration, retinitis pigmentosa, retinal detachments, retinal ischemia, acute retinopathies associated with trauma, inflammatory mediated degenerations, post-surgical complications, the damage associated with laser therapy including photodynamic therapy (PDT), and surgical light induced iatrogenic retinopathy. The compounds are formulated for intraocular, systemic, or topical delivery.

The NR2B antagonists of the present invention may be administered to the eye by chronic or acute regimen. The NR2B antagonists may be administered acutely following acute trauma. In the case of acute administration, the NR2B antagonists of the present invention will be preferably administered intraocularly following traumatic and/or other acute ischemic events involving the retinal and optic nerve head tissues, or prior to or during surgery to prevent ischemic damage or injury.

While intraocular administration methods are preferred, systemic or topical ophthalmic administration of the NR2B antagonists is also contemplated by the present invention.

The NR2B antagonists of the present invention may be contained in various types of pharmaceutical compositions, in accordance with formulation techniques known to those skilled in the art. In general, the NR2B antagonists will be formulated in solutions for topical ophthalmic, intraocular or systemic administration. Solutions, suspensions and other dosage forms adapted for intraocular injection or perfusion, such as balanced salt solutions, are particularly preferred for the acute treatment of retinal and optic nerve head tissues.

When the NR2B antagonists of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus(b Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian et al.), the entire contents of which are incorporated herein by reference. Retrobulbar and periocular injections are known to those skilled in the art and are described in numerous publications including, for example, *Ophthalmic Surgery: Principles of Practice*, Ed., G. L. Spaeth, W.B. Sanders Co., Philadelphia, Pa, U.S.A., pages 85–87 (1990).

In general, systemic administration may be accomplished via oral or intravenous routes known to those skilled in the art. Formulations for such administrations will generally comprise a tablet formulation for oral delivery and an aqueous solution for intravenous injection.

In general, the doses used for the above described purposes will vary, depending on the type and severity of the condition to be treated, the particular improved NR2B antagonist employed as well as the route of administration. However, the improved NR2B antagonists will be included in a composition of the present invention in an effective amount to prevent, reduce or ameliorate retinal or optic nerve head tissue damage. As used herein, the term "pharmaceutically effective amount" refers to an amount of at least one improved NR2B antagonist which will prevent, reduce or ameliorate retinal or optic nerve head tissue damage in a mammal. The doses used for any of the above-described purposes will generally be from about 0.01 nanogram per milliliter (ng/ml) to about 10 microgram per milliliter ($\mu$g/ml) for intraocular infusion or injection. When the compositions are dosed topically to the eye, they will generally be in a concentration range of from 0.001 to about 5% w/v, with 1–2 drops administered 1–4 times per day. Oral or intravenous doses will vary due to possible bioavailability differences of the improved NR2B antagonists.

As used herein, the term "pharmaceutically acceptable carrier" refers to any formulation which is safe and provides appropriate delivery of an effective amount of at least one improved NR2B antagonist for the desired route of administration.

The compositions of the present invention may contain additional pharmaceutically active agents or may be dosed concurrently with other pharmaceutical compositions. In particular, when treating a mammal for the prevention, treatment or amelioration of glaucomatous retinopathy, the compositions of the present invention may contain additional "anti-glaucoma" agents or may be dosed concurrently or sequentially with anti-glaucoma agent compositions. Examples of anti-glaucoma agents include: prostaglandins or prostanoids, carbonic anhydrase inhibitors, beta-adrenergic agonists and antagonists, alpha-adrenergic agonists or other anti-glaucoma agents known to those skilled in the art.

The invention in its broader aspects is not limited to the specific details shown and described above. Departures may be made from such details within the scope of the accompanying claims without departing from the principles of the invention and without sacrificing its advantages.

What is claimed is:

1. A method for the treatment of retinal or optic nerve head damage which comprises administering to a mammal a composition comprising a pharmaceutically effective amount of at least one NR2B antagonist which both inhibits activation of the NR2B receptor and exhibits anti-hypoxia/ischemia efficacy and a pharmaceutically acceptable carrier.

2. The method of claim 1, wherein the NR2B antagonist is selected from the group consisting of: RO-8-4304 and RO-25-6981.

3. The method of claim 1, wherein the composition is an oral, intraocular injection or intraocular irrigating formulation.

4. The method of claim 1, wherein the composition is an oral, intraocular injection or intraocular irrigating formulation.

* * * * *